(12) United States Patent
Jornitz et al.

(10) Patent No.: US 6,666,970 B1
(45) Date of Patent: Dec. 23, 2003

(54) PROCESS AND APPARATUS FOR TESTING FILTRATION UNIT INTEGRITY

(75) Inventors: Maik W. Jornitz, Göttingen (DE); Hans-Jürgen Spanier, Waake (DE)

(73) Assignee: Sartorius AG, Goettingen (DE)

( * ) Notice: Subject to any disclaimer, the term of this patent is extended or adjusted under 35 U.S.C. 154(b) by 0 days.

(21) Appl. No.: 09/980,315

(22) PCT Filed: Jun. 2, 2000

(86) PCT No.: PCT/EP00/05050

§ 371 (c)(1),
(2), (4) Date: Nov. 26, 2001

(87) PCT Pub. No.: WO00/75628

PCT Pub. Date: Dec. 14, 2000

(30) Foreign Application Priority Data

Jun. 8, 1999 (DE) .......................... 199 26 002

(51) Int. Cl.$^7$ ............................ B01D 61/00; G01N 15/08
(52) U.S. Cl. .................... 210/650; 210/741; 210/90; 210/138; 73/38; 73/40; 422/63
(58) Field of Search ................. 210/650, 741, 210/90, 138; 73/38, 40; 324/71.1, 439; 422/63, 43; 436/43; B01D 65/10

(56) References Cited

U.S. PATENT DOCUMENTS 5,552,055 A * 9/1996 Arato ........................ 210/651
5,786,528 A * 7/1998 Dileo et al. ................... 73/38
6,021,661 A * 2/2000 Lowell et al. ................. 73/38

FOREIGN PATENT DOCUMENTS

DE 195 03 311 A1 * 8/1996

* cited by examiner

Primary Examiner—W. L. Walker
Assistant Examiner—K S Menon
(74) Attorney, Agent, or Firm—Chernoff, Vilhauer, McClung & Stenzel, LLP

(57) ABSTRACT

A method and apparatus for conducting water intrusion tests on hydrophobic filtration units is disclosed.

14 Claims, 1 Drawing Sheet

PROCESS AND APPARATUS FOR TESTING FILTRATION UNIT INTEGRITY

This is a 371 of PCT/EP 00/05050 filed Jun. 2, 2000 and the priority of DE 199 26 002.8 filed Jun. 8, 1999 is claimed.

BACKGROUND OF THE INVENTION

The invention concerns a method for testing the integrity of filter units utilizing hydrophobic filter materials by a qualitative water intrusion test and apparatus for carrying out the method.

Such filter units comprise a housing, which is separated by a hydrophobic filter into a feed or inlet side chamber and a permeate or outlet (clean) side chamber. The inlet and outlet side chambers are equipped with fittings, so that the medium to be filtered (gas, hydrophobic liquid) is forced to pass from the inlet to the outlet. Undesirable substances, for example microorganisms, are retained by the filter material. Filter materials may include membranes or non-wovens from the areas of ultrafiltration and microfiltration.

Water intrusion filtration integrity tests on such hydrophobic filtration units are known. Such tests are non-destructive and utilize the characteristic of a hydrophobic filter to reject the entry of water into its pores. Notwithstanding the filter's resistance to the permeation of water, if pressurized water is introduced, the water will then, proportional to the pressure, permeate into the pore structure of the filter. This nearly linear threshold pressure zone is known as an "intrusion zone." If the water pressure is increased, a pressure threshold is reached, at which the permeation of water increases exponentially, known as the "penetration zone." This pressure threshold corresponding to the pressure at which the water breaks through the filter's pores, is affected by the size of the pores of the hydrophobic filter material and may be used to characterize the filter's largest pores. The intrusion zone and penetration zone values for various hydrophobic filter materials are available from filter manufacturers.

To carry out a water intrusion test, the test pressure for the filter material is adjusted to the intrusion zone value and maintained for a specified time. Then, by measuring the pressure drop following said specified time, the amount of water intruded into the pore structure of the filter is measured in terms of per time units. From this intrusion rate measurement conclusions can be drawn in regard to the degree of integrity of the filter material; in the case of intact filter material, the rate of intrusion is very small, while in the case of damaged material, it is correspondingly larger.

In DE 39 17 856 C2 a testing device and a procedure for carrying out an in-line water intrusion test is disclosed. The testing device operates pneumatically and comprises a filter housing for the filter units to be tested as well as the required connection lines and valving. The filter housing, which is fitted with the test filter units, is completely filled with water on the inlet chamber and subsequently subjected to compressed air at a test pressure of 70 to 80% of the penetration zone pressure value that is typical for the filter elements of the test filter units. After a stabilization phase with closed valves, the pressure drop in the system is measured by an upper connection on the filter housing. The disadvantage of this method is that the procedure is too expensive and time-consuming for testing a large number of filter units because each filter unit must be inserted and removed from the filter housing.

In DE 43 39 589 C1 there is also described a quantitative procedure and a test device, which starts with the calculation of those volumes which relate to each test pressure, as compared to a total net volume of the test equipment (determined for a given testing device as a testing device constant).

To avoid large dead volume caused by elongated pressure gas lines, which can lead to errors in pressure readings with variations in temperature, DE 195 03 311 A1 proposes the incorporation of an external electrical pressure sensor at the connection of the filter housing. To monitor and record measurements, this sensor is connected electronically to an evaluation unit. The disadvantage here is that for different types of filter units, either the particular entire net volume must be determined or an external reference container must be employed, which is time-consuming and adds to the complexity and expense of the testing. A further disadvantage is that usable integrity test results can only be obtained when the surface area of the filter unit to be tested is relatively large, because otherwise the pressure drop caused by the water intruding into the filter's pore structure cannot be determined with the necessary precision. Experience has demonstrated that the surface area of filter units to be so tested should be greater than 1000 $cm^2$.

Thus, the present invention has the goal of providing a method for testing the integrity of hydrophobic filter units by a water intrusion test, whereby filter units having smaller surface areas can be simply and routinely tested in large numbers, and further, of providing test apparatus for carrying out said method.

BRIEF SUMMARY OF THE INVENTION

In accordance with the invention, a simple method for testing the integrity of hydrophobic filter units is provided to carry out a qualitative water intrusion test to exclude unusable filter units. A significant advantage to the method is that unusable filter units with serious defects are detected immediately at the start of the test, so there is often no need to continue the test protocol to its end. Another advantage of the method is that it is not limited to tests of filtration units having large surface area filters.

The invention is applicable to testing the integrity of filter units used in the aeration of laboratory fermentations, sterilizers, lyophilizers, sterile tanks and small containers such as glass flasks or for the filtration of hydrophobic liquids.

DETAILED DESCRIPTION OF THE PREFERRED EMBODIMENTS

Figure 1:
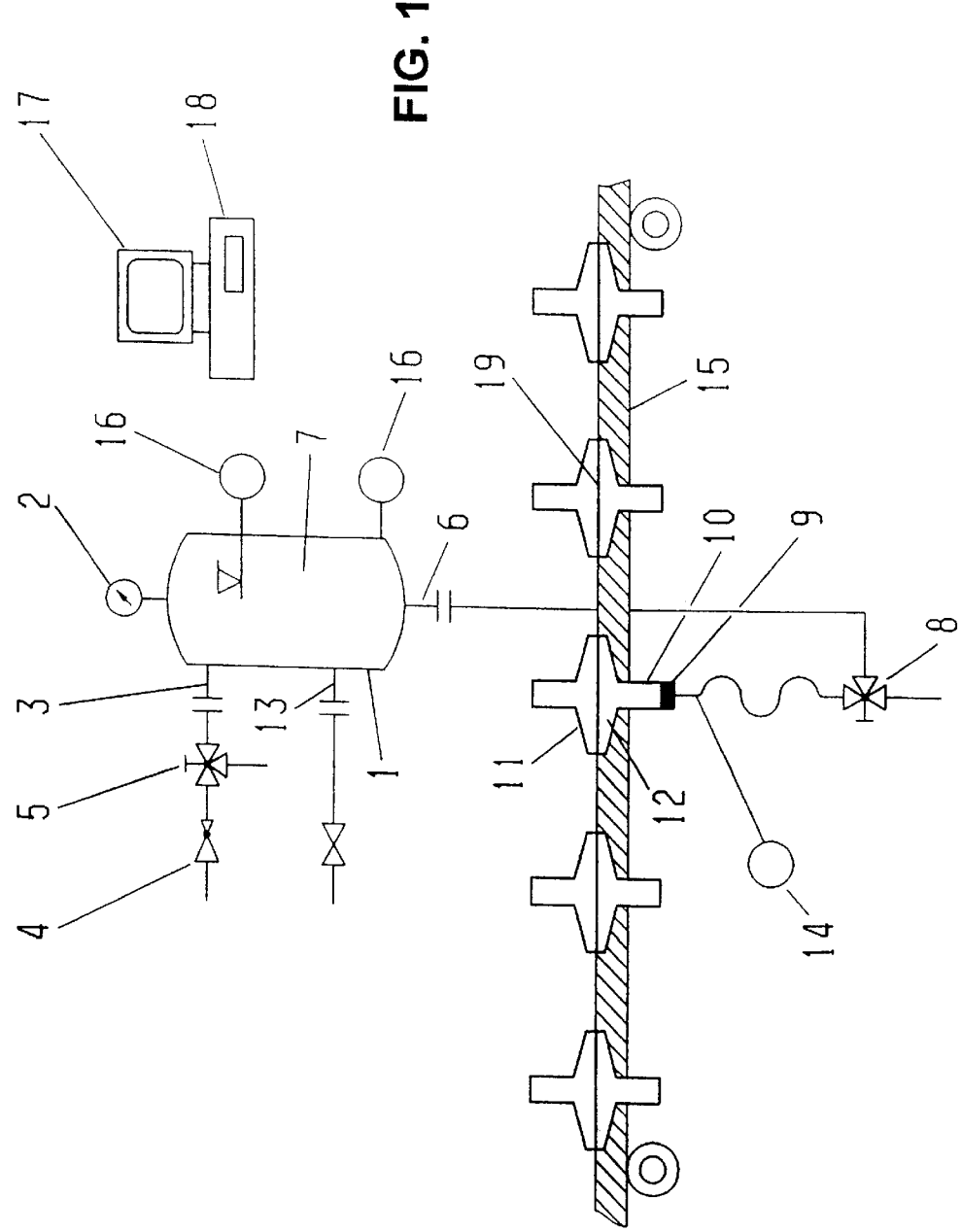
FIG. 1 is a schematic drawing showing an exemplary embodiment of the testing device of the present invention.

Turning to the drawing, there is shown in FIG. 1 an automatically operating testing apparatus comprising a pressure tank 1 equipped with a pressure gauge 2 to measure and monitor the gas test pressure in pressure tank 1. Pressure tank 1 is provided with a connection 3 for the introduction of pressurized gas from a pressurized gas source (not shown). The inflow of gas takes place through a pressure reduction valve 4 and a first three-way valve 5, through which pressurized gas from pressure tank 1 can be vented. Pressure tank 1 is provided with an outlet 6 for the discharge of water 7 through a discharge/feed three-way valve 8 shown in fluid communication with an inlet 10 of a filter unit 11 to be tested, via plug-in station 9. One port of valve 8 permits water 7 to be fed to the inlet chamber 12 of filter unit 11 where it makes contact with hydrophobic filter 19, while another port allows the expulsion of the water after the test is complete. Expelled water from the inlet chamber 12 of filter unit 11 is recycled to pressure tank 1 to partially replace water consumed during the course of the water intrusion tests.

Alternatively, pressure tank 1 can be equipped with a separate valved water replacement line 13 for replenishing the feed of fresh water. Plug-in station 9 is preferably connectable and disconnectable from filter inlet 10 by means of a manipulator 14. A multiplicity of the filter units 11 may be affixed to a filter holder 15 designed as a movable strip. A sensor 16 is installed on pressure tank 1, which assures that a sufficient quantity of water is present in the pressure tank 1. The results of the test may be displayed on a video monitor 17. In an automatically operating mode, the apparatus is preferably equipped with a computer 18 in electronic communication with the measuring and controllable elements of the apparatus including pressure gauge 2, pressurized gas source, valves 4, 5 and 8, the valve in feed replacement line 13, manipulator 14 and video monitor 17.

Utilizing the above-described apparatus, filter units with hydrophobic filters may be tested for integrity, wherein the basic design of the filter unit is such that the hydrophobic filter separates the filter unit housing into inlet and outlet chambers and the fluid to be filtered must pass through the hydrophobic filter from inlet to outlet. The testing method comprises the following steps:

(a) connecting the inlet (10) of the filter unit (11) to be tested with a pressure tank (1) containing, under a cushion of gas, water at a predetermined test pressure, the test pressure being adjusted by a pressure reducer (4) to a value between 40% and 90% of the water penetration pressure typical for that filter unit;

(b) opening a valve (8) between the pressure tank (1) and the inlet (10) of the filter unit (11) to feed water into the inlet (10) of the filter unit's inlet chamber (12), thereby diminishing the test pressure in the pressure tank;

(c) determining whether the test pressure in the pressure tank is restored to its original value within a first time period by the subsequent feed of pressurized gas to the pressure tank through the pressure reducer (4);

(The first time period is dependent upon the configuration of the test apparatus, upon the volume of the gas cushion, and upon the volume of the inlet side housing chamber of the filter unit to be tested. This can readily be measured or calculated in accordance with standard practices in the art.)

(d) if the initial test pressure is not restored within the first time period, omitting steps (e) and (f) and proceeding to step (g);

(If the initial test pressure is not restored within the first time period, this indicates a failure in the integrity of the filter material.)

(e) after the initial test pressure in the pressure tank is restored, and after the elapse of a stabilization time period, discontinuing the feed of pressurized gas to the pressure tank;

(The stabilization time period is typically less than three minutes and depends upon the configuration of the tested filter unit and its filter material. In the case of filtration units with pleated filter material such as is employed in cartridges, because of the greater surface area the stabilization period is longer than in the case of filtration units with flat filters.)

(f) determining whether the test pressure is maintained or is reduced after the elapse of a second time period; and (A reduction in the test pressure indicates a failure in the integrity of the filter material. In order to achieve a reliable and comparable result, the second time period should be observed empirically to establish a control for each type of filter unit. In general the test will be reliable if the second time period is within the range of about 0.25 to about 3 minutes.)

(g) disconnecting the inlet of the filter unit from the pressure tank.

In a preferred version of the method, failure of the filter's integrity after conducting steps (d) or (f) is indicated by an audio or visual signal.

In a further embodiment of the invention, it is advantageous if step (a) is conducted by connecting the inlet 10 of the filter unit 11 to plug-in station 9, shown schematically in FIG. 1, wherein station 9 is in fluid communication with pressure tank 1 by way of a flexible pressure line, shown schematically by the wavy line in the lower portion of FIG. 1.

In a preferred embodiment of the invention, the test filter unit 11 is mounted in a filter holder 15 prior to its connection with pressure tank 1. Such an arrangement is particularly advantageous when the connection and the disconnection of the filter unit to and from either the pressure tank 1 or the plug-in station 9 is conducted by a manipulator 14, shown schematically in FIG. 1.

In yet another preferred embodiment, when a large number of filter units are routinely tested, then a multiplicity of the filter units may be affixed to filter holder 15, such as shown schematically in FIG. 1, and are connected seriatim to the pressure tank for each filter unit's integrity test, either directly or via plug-in station 9.

It is particularly preferred that the inlet 10 of the test filter unit 11 is pointed downwards so that when the inlet chamber 12 is filled with water no gas cushion can form therein because any gas present escapes through the pores of the hydrophobic filter element before the surface of the filter element is completely covered by water, and this water coating acts as a gas (air) barrier. An additional advantage of mounting the inlet 10 of the test filter unit 11 downwardly is that when the test is complete and the unit is disconnected from the testing apparatus, water flows by gravity out of inlet chamber 12.

In another embodiment of the inventive method, the filter units are so affixed to the filter holder that the hydrophobic filter deviates from the horizontal, thereby permitting the inlet of the filter units to be directed upwardly without creating a gas barrier layer on the surface of the filter element, which would hinder the full escape of the gases out of the inlet chamber 12. Filter holder 15 can be designed as a linear strip as shown schematically in FIG. 1, as a disk, as a vertical compartmental conveyor, or as an elevator device, and moved incrementally so that each test filter unit is presented seriatum to plug-in station 9. Alternatively plug-in station 9 may itself be transported to the inlet 10 of a stationary filter unit 11 by a manipulator 14.

In another advantageous embodiment, the pressure gauge 2 is provided with means for transmitting a signal, preferably an audible and/or visible signal, which gives notice of failure of the integrity test. Plug-in station 9 is selected so as to be compatible with the particular inlet fitting of the test filter unit, e.g., to accommodate the end of a pressure hose or a Luer-Lock-type connector.

For routine testing of a multiplicity of filter units, the testing apparatus is preferably equipped with filter holders that keep the test filter units stationary. As mentioned above, the filter holders may move intermittently as a strip, a disk, as vertically circulating compartments or as an elevator-type conveyor. After conclusion of the testing procedure these filter holders are then moved step-wise, either manually or by an incrementally stepping motor, so that each time the new filter unit 11 to be tested is presented to the plug-in station 9 of the of the pressure tank 1, a manipulator 14 can make a fluid-tight connection between the inlet 10 of the filter unit 11 and the plug-in station 9, or conversely, can release the plug-in station from the inlet of the filter unit.

The pressure tank is preferably equipped with a sensor 16 to monitor the level of the water therein so as to assure that sufficient water is available in the tank to carry out the testing. Sensor 16 can be in electronic communication with an inlet valve in water replacement line 13 to pressure tank 1 so as to open the valve when sensor 16 senses a low water level, thereby allowing for automatic fill of the pressure tank. The water used in the integrity tests should be of at least reverse osmosis (RO) quality. A temperature control for the water would also be of advantage in assuring a high degree of consistency in the test results.

In an especially preferred embodiment of the invention, the test apparatus is made to be completely automatic in carrying out the testing method. This is possible by making the apparatus computer-controlled by allowing electronic communication between a computer and the valves, the pressure-measuring equipment, the monitoring devices for the water supply, the manipulator, the filter-holder, a failure signal and a video display.

EXAMPLE 1

The integrity of a Midisarta filter unit (from Sartorius AG of Goettingen, Germany) with a flat filter of a hydrophobic polytetrafluoroethylene (PTFE) membrane having a pore size of 0.2 $\mu$m and a filtering surface area of about 20 cm$^2$ was tested by the inventive method using apparatus of substantially the same design shown in FIG. 1. The inlet 10 the test filter unit 11 was connected to a pressure tank 1 containing about 5 L of RO-quality water under an air cushion having a volume of about 100 mL, at a test pressure of 2500 mbar. According to the manufacturer's specifications the water penetration pressure for the filter unit was 5 bar. A valve 8 between the pressure tank 1 and the inlet 10 of the test filter unit 11 was opened, causing water to flow into the filter unit's inlet chamber 12. A pressure reducer 4 had been adjusted so that after no more than 15 seconds (the first time period of step (c) was set at 20 seconds), the test pressure of 2500 mbar would b e reached if the filter unit did not possess any severe defects. The 2500 mbar test pressure was not achieved even after 20 seconds, and water was observed to be weeping from the out let of the test filter unit, indicating failure of integrity.

EXAMPLE 2

Example 1 was substantially repeated, but this time the test pressure was achieved within 20 seconds. The test pressure was maintained for a stabilization time period of 30 seconds by closing a valve 5 between the pressure reducer 4 and pressure tank 1, thereby interrupting the gas feed to the pressure tank. Based upon previous empirical observations, the second time period of step (f) was determined to be one minute; after the lapse of this second time period the test pressure was observed to decline, indicating a failure of the integrity of the test filter unit.

EXAMPLE 3

Example 2 was substantially repeated with the exception that the test pressure remained constant after the passage of the second time period of one minute, indicating that the integrity of the filter material had passed the test.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method of testing the integrity of at least one filter unit (11) having a hydrophobic filter (19) by a water intrusion test, comprising the following steps:
    (a) connecting said at least one filter unit (11) to a filter holder (15) capable of connecting to a multiplicity of filter units (11) and capable of incremental movement so as to present a multiplicity of filter units (11) one at a time to a plug-in station (9),
    (b) connecting said at least one filter unit (11) to a pressure tank (1) via said plug-in station (9) and a flexible pressure line that are in fluid communication with said pressure tank (1), said pressure tank (1) containing water at an initial predetermined test pressure under a cushion of gas;
    (c) reducing said test pressure in said pressure tank (1) to a value that is between 40% and 90% of the water penetration pressure for said at least one filter unit (11);
    (d) placing said pressure tank (1) in fluid communication with said feed inlet (10) so as to cause (i) water to flow into said inlet chamber (12) and (ii) the test pressure to diminish in said pressure tank (1);
    (e) introducing gas to said pressure vessel (1) for a predetermined first time period to increase the test pressure therein;
    (f) determining whether the test pressure in said pressure tank (1) is restored to its initial predetermined level within said first time period;
    (g) if the test pressure in said pressure tank (1) is not restored to its initial predetermined level within said first time period, omitting steps (h) and (i) and proceeding directly to step (j);
    (h) discontinuing the introduction of gas to pressure tank (1) after the test pressure has been restored to its initial predetermined level and after the elapse of a predetermined stabilization time period;
    (i) determining whether the test pressure is maintained or declines within a predetermined second time period; and
    (j) interrupting the fluid communication between said pressure tank (1) and said inlet (10) and releasing the connection between said at least one filter unit (11) and said pressure tank (1) by removing said at least one filter unit (11) from said plug-in station (9).

2. The method of claim 1 including the use of a signal to indicate the occurrence of (i) the test pressure not being restored in step (g) and (ii) the decline of the test pressure in step (i).

3. The method of claim 2 wherein said signal is selected from an audible signal and a visual signal.

4. The method of claim 1 wherein a multiplicity of filter units (11) are tested one at a time.

5. The method of claim 4 Wherein each of said multiplicity of filter units (11) are successively connected to said plug-in station (9).

6. The method of claim 1 wherein said at least one filter unit (11) is affixed to said filter holder (15) so that said hydrophobic filter (19) is oriented at an angle relative to horizontal.

7. The method of claim 5 wherein said filter holder (15) is moved in increments to present each filter unit (11) to said plug-in station (9) one at a time.

8. The method of claim 1 wherein step (b) is conducted by a manipulator (14).

9. Apparatus for testing the integrity of at least one filter unit (11) having a hydrophobic filter by a water intrusion test, comprising:

(a) a pressure tank (1) having a pressure gauge (2) and a pressurized gas conduit (3) and a pressurized water conduit (6) in fluid communication with said pressure tank, said pressure tank being capable of holding said water under a gas cushion;

(b) closable connections in said pressurized gas conduit (3) comprising a pressure reducer (4) and a valve (5);

(c) a closable connection in said pressurized water conduit comprising a valve (8) in fluid communication with (d) a flexible pressure line and a plug-in station (9) for attaching said at least one filter unit (11) thereto; and (e) a filter holder (15) adapted to accommodate a multiplicity of filter units (11) and provided with incremental movement capacity so as to present a multiplicity of filter units (11) one at a time to said plug-in station (9).

10. The apparatus of claim 9 wherein said pressure gauge (2) is capable of providing a signal to indicate a failure of the integrity of said at least one filter unit (11).

11. The apparatus of claim 9 wherein said filter holder (15) has a design selected from a strip, a disk, a series of vertically rotating compartments and an elevator.

12. The apparatus of claim 9 including a manipulator (14) capable of placing said at least one filter unit (11) in fluid communication with said plug-in station (9).

13. The apparatus of claim 9 wherein said pressure tank is equipped with a sensor (16) capable of sensing the level of the water therein.

14. The apparatus of any of claims 9–13 including a computer (18) in electronic communication with and capable of monitoring and controlling pressure gauge (2), valves (5,8), manipulator (14), and sensor (16).

* * * * *

UNITED STATES PATENT AND TRADEMARK OFFICE
CERTIFICATE OF CORRECTION

PATENT NO. : 6,666,970 B1
DATED : December 23, 2003
INVENTOR(S) : Jornitz et al.

It is certified that error appears in the above-identified patent and that said Letters Patent is hereby corrected as shown below:

Column 5,
Line 6, delete "of the" (second occurrence) in "of the of the pressure tank".
Line 31, change "Midisarta" to -- Midisart® --.
Line 37, change "the" (second occurrence) to -- of --.
Line 47, delete space between "b" and "e" in "would b e reached" so it reads
-- would be reached --.
Line 50, delete space between "out" and "let" in "from the out let of the test filter" so it reads -- from the outlet of the test filter --.

Column 6,
Line 18, delete the comma "," after "station (9)" and insert a semi-colon -- ; -- so it reads
-- station (9); --.

Signed and Sealed this

Thirtieth Day of November, 2004

JON W. DUDAS
*Director of the United States Patent and Trademark Office*